United States Patent [19]
Weng et al.

[11] Patent Number: 5,512,300
[45] Date of Patent: Apr. 30, 1996

[54] PREVENTION OF IBUPROFEN FROM FORMING LOW MELTING EUTECTICS WITH OTHER THERAPEUTIC AGENTS IN SOLID DOSAGE FORMS

[75] Inventors: Timothy H. Weng, Randolph; Michael G. Williams, Flanders, both of N.J.

[73] Assignee: Warner-Lambert Company, Morris Plains, N.J.

[21] Appl. No.: 945,203

[22] Filed: Sep. 15, 1992

[51] Int. Cl.⁶ .................. A61K 9/10; A61K 9/14; A61K 9/16; A61K 9/20
[52] U.S. Cl. .............. 424/465; 424/464; 424/484; 424/489; 514/770; 514/771; 514/970
[58] Field of Search .................. 424/464, 465, 424/468, 484, 489; 514/960

[56] References Cited

U.S. PATENT DOCUMENTS

| | | | |
|---|---|---|---|
| 4,145,440 | 3/1979 | Fitch et al. | 514/781 |
| 4,610,875 | 9/1986 | Panoz et al. | 424/80 |
| 4,753,800 | 6/1988 | Mozda | 424/441 |
| 4,769,236 | 9/1988 | Panoz et al. | 424/80 |
| 4,937,080 | 6/1990 | Appelgren et al. | 424/468 |
| 5,075,291 | 12/1991 | DuRoss | 424/440 |

FOREIGN PATENT DOCUMENTS

| | | |
|---|---|---|
| 0159852 | 10/1985 | European Pat. Off. |
| 1-309372 | 10/1989 | Japan . |
| 3-023095 | 1/1991 | Japan . |

OTHER PUBLICATIONS

Kararli et al., "Solid–State Interaction of Magnesium Oxide and Ibuprofen to Form a Salt," Pharmaceutical Research, vol. 6, No. 9, 1989, 804–808.

*Primary Examiner*—Carlos Azpuru
*Assistant Examiner*—James M. Spear
*Attorney, Agent, or Firm*—Michael J. Atkins

[57] ABSTRACT

A method for preparing ibuprofen granulations which exhibit improved stability and resistance to the formation of low melting point eutectics is disclosed. The method includes forging an amalgamation of ibuprofen and an alkali metal in a physical matrix which is suitable for inclusion in a composition without destroying the amalgamation. The stabilized ibuprofen granulation can be combined with other active ingredients and/or excipients to form compositions which have extended shelf life and are resistant to the formation of low melting point eutectics.

22 Claims, 3 Drawing Sheets

PREVENTION OF IBUPROFEN FROM FORMING LOW MELTING EUTECTICS WITH OTHER THERAPEUTIC AGENTS IN SOLID DOSAGE FORMS

BACKGROUND OF THE INVENTION

The present invention relates to pharmaceutical formulations containing ibuprofen and methods for producing the same. More particularly, the present invention involves a method for preparing improved ibuprofen granulations.

It has been recognized that solid dosage forms such as tablets containing ibuprofen and other ingredients tend to exhibit stability problems, including the formation of low melting point eutectics. In general, eutectic compositions often exhibit unique physical properties such as melting or freezing points which are not characteristic of the individual constituents. For example, eutectic compositions composed of two constituents having different melting points may have melting point which is lower than either of the constituents. In some cases, the unique physical properties of a eutectic composition are desirable. For example, eutectic compositions of two or more metals are frequently used in low melting point solders in order to incorporate the strength or some other property of one metal with a desirable quality found in a second metal.

Alternatively, the physical properties exhibited by some eutectic compositions can be undesirable. In particular, certain pharmaceutical formulations can form eutectic compositions which exhibit undesirable melting point depressions. It is recognized in the art that these melting point depressions may significantly impair the stability of the formulation. In some cases, eutectic compositions occur immediately upon intimate association of the constituents present in a formulation. Alternatively, some formulations develop a eutectic character after the constituents have been in intimate contact with one another for a prolonged period of time. Other formulations develop a eutectic character after having undergone exposure to certain environmental conditions, such as fluctuations in temperature, pressure or humidity.

In particular, it has been found that certain ibuprofen-containing solid dosage forms such as powders, granules, pellets, capsules, tablets and the like exhibit stability problems. It is further recognized that the instability of such dosage forms is at least in part attributable to the tendency of these formulations to undergo undesirable melting point depressions. For example, although the melting point of ibuprofen is approximately 75° C., formulations containing ibuprofen and terfenadine melt at temperatures ranging from about 50° to about 75° C. This melting point depression phenomena is thought to be attributable to the tendency of ibuprofen to form eutectic compositions with certain substances. Ibuprofen also forms low melting point eutectics with substances such as diphenhydramine hydrochloride and astemizole.

Eutectic formations, however, significantly reduce the shelf-life of ibuprofen-containing products. For example, many prior art tablets containing ibuprofen and other active ingredients and/or excipients tend to exhibit structural deteriorations such as crumbling, pitting and fissuring, as well as a loss of color as a result of the eutectic formation. Alterations in the crystalline structures. have also been observed.

Some ibuprofen-containing formulations tend to exhibit melting point depressions almost immediately. Other formulations are stable initially but undergo changes in consistency upon exposure to fluctuations in temperature and/or other environmental factors. Still other ibuprofen-containing formulations may inherently develop these melting point depressions upon prolonged intimate contact of the ibuprofen with the other constituents present in the formulations. Each of these situations create storage problems. Consequently, there is a need to develop methods for preparing stable ibuprofen-containing formulations.

It is therefore an object of the present invention to provide new methods of preparing ibuprofen granulations.

It is also an object of the present invention to provide an improved method for preparing solid dosage forms containing ibuprofen in combination with other ingredients.

SUMMARY OF THE INVENTION

The present invention is directed to methods for preparing stabilized ibuprofen. Granulations containing the stabilized ibuprofen resist eutectic reactions when combined with other active ingredients or excipients. The method involves forging an amalgamation of ibuprofen and an alkali metal in a physical matrix which is suitable for inclusion in a composition without disrupting the amalgamation. The amalgamation is forged preferably by heating ibuprofen to form a melt, adding an alkali metal to the melt and mixing the constituents until a homogenous paste is formed. The alkali metal is preferably provided in the form of magnesium, calcium, potassium, aluminum or sodium compounds or salts. The paste is cooled to solidification, reduced to a predetermined particle size and thereafter dried.

The granulation can be combined with other active ingredients such as antihistamines and/or suitable excipients in order to form various ibuprofen-containing formulations. The formulations can be in the form of powders, granules, pellets, capsules, tablets and the like.

The method of the present invention advantageously provides ibuprofen granulations which are resistant to the undesirable melting point depressions frequently observed in prior art ibuprofen-containing formulations. The ibuprofen-containing formulations of the present invention also exhibit increased stability and have improved shelf-life.

For a better understanding of the present invention, together with other and further objects, reference is made to the following description and the accompanying drawings, the scope of which will be pointed out in the appended claims.

DETAILED DESCRIPTION OF THE INVENTION

Figure 1:
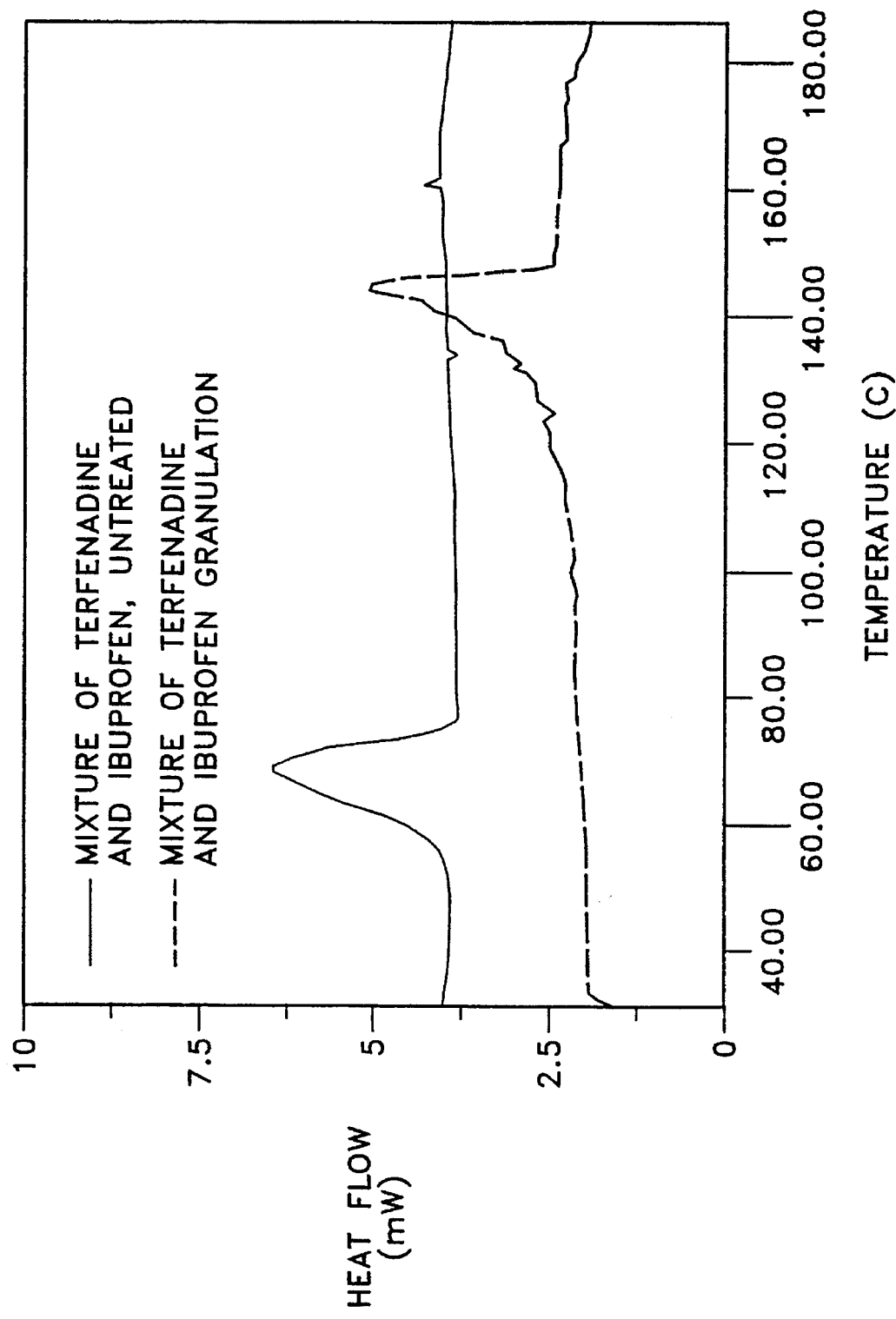
FIG. 1 is a thermogram comparing the melting point of a formulation containing terfenadine and untreated ibuprofen with that of a formulation containing terfenadine and an ibuprofen granulation prepared in accordance with the present invention.

The present invention includes a method of preparing stabilized ibuprofen granulations. The granulations can be incorporated into several solid formulations, such as powders, granules, pellets, capsules, tablets and the like. The present method includes forging an amalgamation between ibuprofen and an alkali metal. The method further includes heating ibuprofen to form a melt without inducing any undesirable heat-associated degradation. In this regard temperatures of from about 75° to about 95° C. are preferred. In a preferred embodiment, a steam-jacketed reaction vessel may be used to form the melt.

Once the ibuprofen is melted, an alkali metal is added to the melt. The alkali metal is preferably mixed with the melt with sufficient agitation for an adequate length of time in order to maximize the distribution and the contact time with the ibuprofen. For example, in order to prepare 850 grams of ibuprofen-containing granulation, an alkali metal-containing compound, such as magnesium hydroxide paste, should be mixed with the melt for at least a ten minute period.

The alkali metal is preferably added as a paste containing an alkali metal compound. Alternatively, alkali metal-containing compounds may be added in the form of a solution, slurry, dry particulate or powder. Most compounds or salts containing an alkali metal may be selected as the source of the alkali metal so long as the compound or salt is capable of reacting with the ibuprofen in situ to forge the amalgamation. Compounds or salts containing magnesium, calcium and sodium are preferred. Examples of suitable compounds or salts include magnesium hydroxide, magnesium oxide, magnesium carbonate, magnesium carbonate hydroxide, potassium hydroxide, potassium carbonate, potassium bicarbonate, sodium hydroxide, sodium carbonate, sodium bicarbonate, calcium hydroxide, calcium oxide, calcium carbonate, aluminum oxide, aluminum hydroxide, aluminum magnesium hydroxide, aluminum potassium oxide, aluminum sodium oxide, aluminum sodium carbonate hydroxide and mixtures thereof. Magnesium hydroxide is most preferred.

In the present invention an amalgamation is forged when ibuprofen and an alkali metal are intimately contacted so that a relationship of the chemical and physical properties of the ibuprofen and alkali metal is formed which results in stabilization of the ibuprofen in a composition. The amalgamation must also include a physical matrix suitable for inclusion in a composition without disrupting the stabilizing relationship. It has been found that such an amalgamation can be forged by forming a homogeneous paste with ibuprofen and the alkali metal. Other methods of forging the amalgamation may exist, and it is intended to include all such methods which provide the necessary component relationships and physical matrix.

While not being bound by theory, the amount of alkali metal and alkali metal-containing compound needed for the stabilizing amalgamation is believed to be dependent upon the number of alkali metal atoms present in the alkali metal compound, the valence state of the metal atoms and the amount of ibuprofen present. Generally, the amount of alkali metal-containing compound added to the ibuprofen melt should be calculated so that the number of molecules of the alkali-metal-containing compound present is about equal to or greater than the following:

$$\frac{Z}{A \cdot C} \text{ or } \frac{Z_1}{A_1 C_1 + \ldots + A_n C_n}$$

wherein:
- Z represents the number total of ibuprofen molecules present in the melt;
- A represents the number of alkali metal atoms or alkali metal-containing cations;
- C represents the valence state of the alkali metal atom or alkali metal-containing cation; and
- where 1 . . . n represents various alkali metals in the event that more than one is used to effect the amalgamation.

In any event, the amalgamation forged between the ibuprofen and alkali-metal provides a stabilized composition which resists forming low melting point eutectics. For example, if calcium carbonate ($CaCO_3$) is used as the alkali-metal containing compound, the amount should be such that the number of $CaCO_3$ molecules is about equal to or greater than the number of ibuprofen molecules divided by 2, since there is only one calcium atom present (A=1) and since the calcium has a valence state of +2 (C=2).

Similarly, if potassium oxide ($K_2O$) is used as the alkali-metal containing compound, the amount should be such that the number of $K_2O$ molecules is about equal to or greater than the number of ibuprofen molecules divided by 2, since there are 2 potassium atoms present (A=2) and since the potassium has a valence state of +1 (C=i).

In view of the foregoing, the alkali metal-containing compound is present in an amount ranging from about 1% to about 90% by weight of the dried ibuprofen granulation (or from about 0.5% to about 100% by mole of the ibuprofen granulation). More preferably, the alkali metal-containing compound is present in an amount ranging from about 3% to about 50% by weight of the dried granulation (or from about 10% to about 100% by mole of the ibuprofen granulation. previously mentioned, the alkali metal-containing compound may be provided in a paste, slurry, solution, dry particulate or powder form.

Once the alkali metal-containing compound has been added to the ibuprofen melt, the ingredients are mixed until a homogenous, creamy paste is formed. Mixing may be accomplished using any of several mixing apparatus known in the art, such as a Hobart mixer. Preferably, the ingredients are kept in a melted form during mixing, taking care to while avoid unnecessary heat degradation. Mixing times will vary depending upon the form of the alkali metal-containing compound, the chemical and physical properties of the metal-containing compound, the volume of the constituents to be mixed and the like. For example, magnesium hydroxide powder tends to require more mixing time when compared to slurries or pastes of the same compound.

The homogeneous ibuprofen-alkali metal paste is then cooled to solidification. Preferably, mixing is continued during cooling. Cooling can be accomplished by any means known in the. art, such as for example using a water jacket around the reaction vessel.

The solidified mass is thereafter reduced to granule size. The sizing can be accomplished by any of several methods known in the art, such by screening. The granules may have a particle size of from about 8 to about 325 mesh with sizes of about 30 mesh being preferred. Thereafter, the granules are dried.

Drying may be carried out at temperatures ranging from about 30° C. to about 100° C. and preferably from about 40° C. to about 80° C. The most preferred temperature range is from about 60° C. to about 70° C. The drying time will depend upon factors such as the drying temperature selected and batch size. Prolonged drying times approaching 18 to 24 hours are advantageous since they promote the amalgamation between the ibuprofen and the alkali metal. In this regard, slow-drying ovens rather than a quick-drying, fluid-bed apparatus are preferred. The dried granules should have a moisture content of less than about 4% by weight and preferably less than about 2% by weight water.

The dried ibuprofen granules can be combined with other substances including medicaments, various excipients and the like in order to prepare various solid-formulations including tablets, powders, pellets and capsules using procedures well-known in the art. For example, compressed tablets can be prepared containing the ibuprofen granules of the present invention along with antihistamines, decongestants, anti-cholinergics, diuretics, antacids, $H_2$ antagonists, prostaglandins, analgesics, anti-tussives, stimulants, expectorants, anesthetics and combinations thereof.

For example, suitable antihistamines include terfenadine, astemizole, diphenhydramine, chlorpheniramine maleate, brompheniramine maleate, triprolidine and the like. Examples of suitable decongestants include phenylpropanolamine, phenylephrine hydrochloride, pseudoephedrine hydrochloride and the like. Examples of suitable analgesics include acetaminophen, codeine, propoxyphene, hydrocodone and the like.

The resulting ibuprofen-containing formulations show greatly improved resistance to the formation of low melting eutectics. The products also exhibit exceptional stability and have extended shelf-lives.

The following Examples serve to provide further appreciation of the invention but are not meant in any way to restrict the effective scope of the invention.

EXAMPLE 1

In this Example, 800 grams of ibuprofen was melted in a Hobart mixer at 80° to 90° C. 383.5 grams of magnesium hydroxide paste was added into the melted ibuprofen with mixing. The magnesium hydroxide paste consisted of 29.5% by weight of magnesium hydroxide and 70.5% by weight of water. The mixture was blended for 10 minutes and then cooled to room temperature. The granulation was sized through a 30 mesh screen and subsequently dried in a drying oven at 60° to 65° C. for 22 hours.

The resulting dried ibuprofen granules were mixed with 240 grams of the antihistamine terfenadine. The resulting formulation could be mixed with other active ingredients and/or excipients before being placed in capsules or compressed into tablets.

Referring now to FIG. 1, there is provided a thermogram comparing the melting point of Formulation A, containing terfenadine and untreated ibuprofen, with that of Formulation B, containing terfenadine and the ibuprofen granulation prepared above. Formulation A, containing the untreated ibuprofen, had a melting point ranging from about 50° to about 75° C. Formulation B on the other hand containing the stabilized ibuprofen granulation of the present invention had a melting point ranging from about 110° to about 150° C., clearly indicating its resistance to the formation of low melting point eutectics.

EXAMPLE 2

In this Example, stabilized ibuprofen granules were prepared following the procedure set forth in Example 1. The ibuprofen granulation was thereafter mixed with 100 grams of diphenhydramine hydrochloride. The resulting formulation was ready for further mixing with other constituents if necessary before being encapsulated or compressed into tablets.

Figure 2:
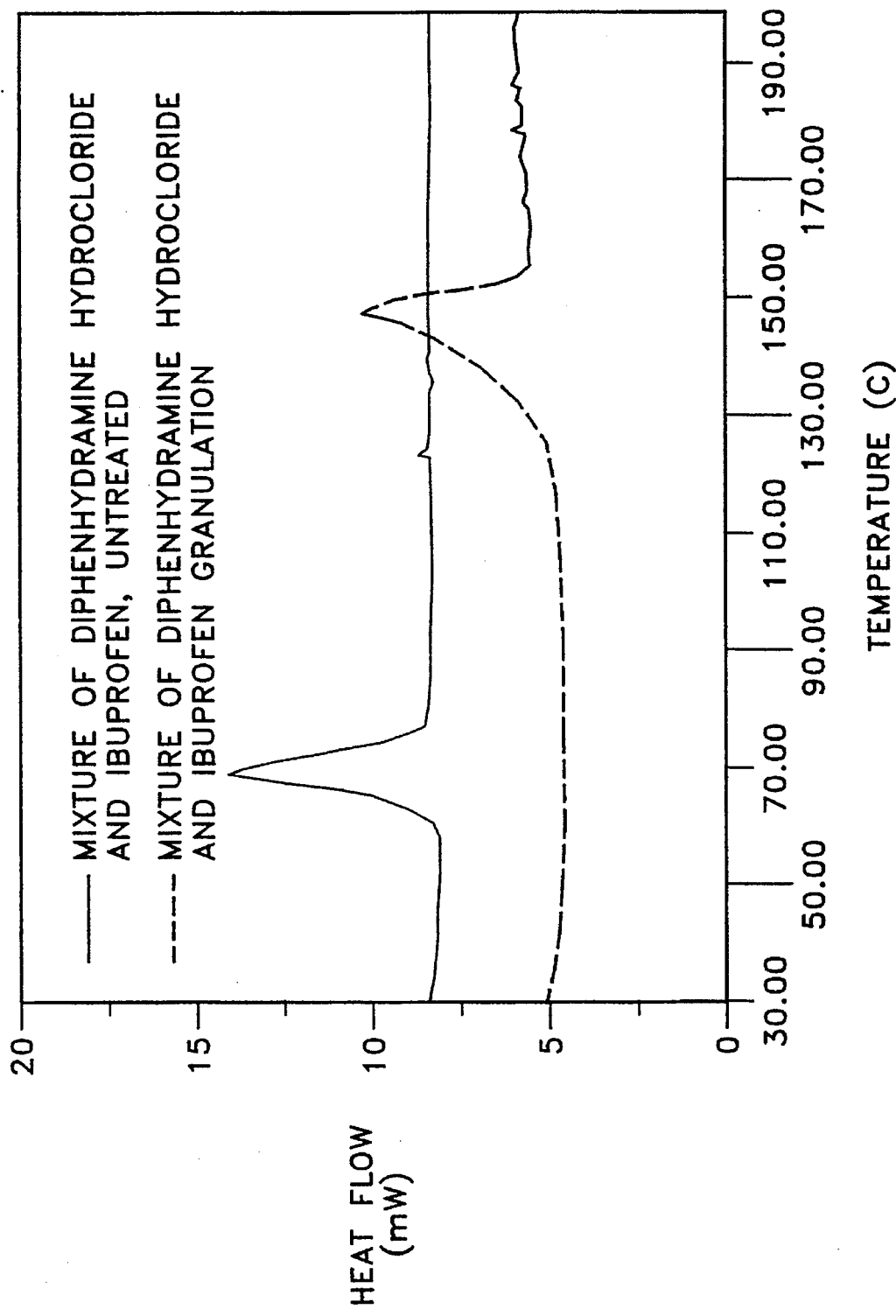
FIG. 2 is a thermogram comparing the melting point of a formulation containing diphenhydramine hydrochloride and untreated ibuprofen with that of a formulation containing diphenhydramine hydrochloride and an ibuprofen granulation prepared in accordance with the present invention.

Referring now to FIG. 2, a thermogram is provided comparing the melting point of Formulation C, containing diphenhydramine hydrochloride and untreated ibuprofen, with that of Formulation D, containing diphenhydramine hydrochloride and the ibuprofen granulation prepared by the method of the present invention. Formulation C, containing the untreated ibuprofen had a melting point ranging from about 55° to about 75° C. whereas Formulation D, containing the stabilized ibuprofen had a melting point ranging from about 120° to about 155° C. Thus, the stabilized ibuprofen clearly demonstrated its resistance to the formation of low melting point eutectics.

EXAMPLE 3

In this Example, ibuprofen granules were again prepared following the procedure set forth in Example 1. The stabilized ibuprofen granules were mixed with 40 grams of the antihistamine astemizole in the manner set forth above. The resulting formulation was compared to a formulation containing untreated ibuprofen.

Figure 3:
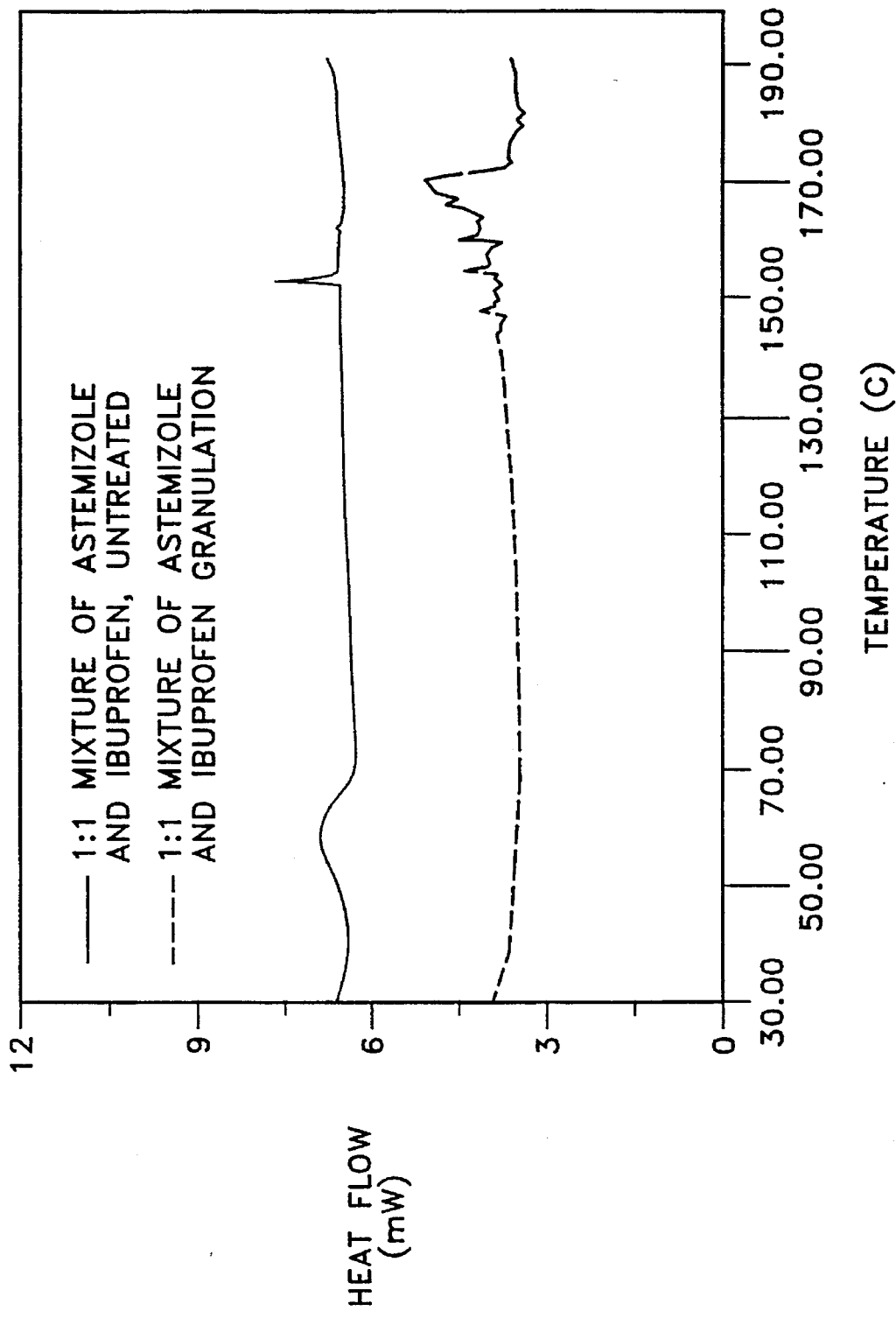
FIG. 3 is a thermogram comparing the melting point of a formulation containing astemizole and untreated ibuprofen with that of a formulation containing astemizole and an ibuprofen granulation prepared in accordance with the present invention.

Referring to FIG. 3, a thermogram comparing the melting point of Formulation E, containing astemizole and untreated ibuprofen, with that of Formulation F, containing astemizole and stabilized ibuprofen granules is provided. The thermogram shows Formulation E had a melting point ranging from about 40° to about 70° C. whereas inventive Formulation F had a melting point ranging from about 145° to about 170° C., again clearly indicating a marked resistance to the formation of low melting point eutectics.

As a result of the method of the present invention, improved formulations containing ibuprofen and other active ingredients and/or excipients can be prepared which do not exhibit undesirable melting point depressions and have a significantly increased shelf-life. Additionally, the increased stability exhibited by the ibuprofen-containing formulations produced by the method of the present invention provide for an ibuprofen product which is resistant to structural deterioration, thus promoting marketability.

Although illustrative embodiments of the present invention have been described herein with reference to the accompanying drawings, it is to be understood that the invention is not limited to those precise embodiments, and that various other changes and modifications may be incorporated therein by one skilled in the art without departing from the scope or spirit of the invention.

What is claimed is:

1. A method of stabilizing ibuprofen for use in a composition comprising:
   a) directly heating ibuprofen to form a melt;
   b) combining said ibuprofen melt with an alkali metal to forge an amalgamation; and
   c) mixing the ibuprofen melt with the alkali metal to form a homogenous paste suitable for inclusion in a composition without disrupting said amalgamation.

2. A method according to claim 1, further comprising performing said mixing at a temperature from about 75° to about 95° C.

3. A method according to claim 1, further comprising solidifying said homogeneous paste to form a solid and reducing said solid to granules.

4. A method according to claim 1, further comprising selecting said alkali metal from the group consisting of calcium, magnesium, sodium, potassium and aluminum.

5. A method according to claim 4, further comprising providing said alkali metal in an alkali metal-containing compound.

6. A method according to claim 5, further comprising selecting said alkali metal-containing compound from the group consisting of magnesium hydroxide, magnesium oxide, magnesium carbonate, magnesium carbonate hydroxide, potassium hydroxide, potassium carbonate, potassium bicarbonate, sodium hydroxide, sodium carbonate, sodium bicarbonate, calcium hydroxide, calcium oxide, calcium carbonate, aluminum oxide, aluminum hydroxide, aluminum magnesium hydroxide, aluminum potassium oxide, aluminum sodium oxide, aluminum sodium carbonate hydroxide and mixtures thereof.

7. A method according to claim 6, further comprising selecting magnesium hydroxide as said alkali metal-containing compound.

8. A method according to claim 5, further comprising drying said homogenous paste, thereby forming a dry ibuprofen-containing granulation.

9. A method according to claim 8, further comprising providing said alkali metal-containing compound in an amount such that it provides from about 1% to about 90% by weight of said dry granulation.

10. A method according to claim 9, further comprising providing said alkali metal-containing compound in an amount such that it provides from about 5% to about 50% by weight of said dry granulation.

11. A method according to claim 5, further comprising providing said alkali metal-containing compound in a paste form.

12. A method according to claim 5, further comprising providing said alkali metal-containing compound in a slurry form.

13. A method according to claim 5, further comprising providing said alkali metal-containing compound in a solution form.

14. A method according to claim 5, further comprising providing said alkali metal-containing compound in a powder form.

15. A method according to claim 5, further comprising providing said alkali metal-containing compound in a dry particulate form.

16. A method according to claim 3, further comprising drying said granules to a moisture content of less than about by weight of water.

17. A method according to claim 16, further comprising performing said drying at a temperature from about 30° to about 100° C.

18. A method according to claim 17, further comprising performing said drying at a temperature from about 40° to about 80° C.

19. A method according to claim 18, further comprising performing said drying at a temperature from about 60° to about 70° C.

20. A method according to claim 3, further comprising compressing said granules into a solid dosage form.

21. A method according to claim 20, further comprising including a medicament in said solid dosage form.

22. A method according to claim 21, further comprising selecting said medicament from the group consisting of antihistamines, decongestants, anti-cholinergics, diuretics, antacids, $H_2$ antagonists, prostaglandins, analgesics, antitussives, stimulants, expectorants, anesthetics and combinations thereof.

* * * * *